United States Patent [19]

Marble et al.

[11] Patent Number: 5,700,667
[45] Date of Patent: Dec. 23, 1997

[54] STRATEGY FOR THE PRODUCTION OF RNA FROM IMMOBILIZED TEMPLATES

[75] Inventors: Herbert A. Marble; Robert H. Davis, both of Boulder, Colo.

[73] Assignee: Regents of the University of Colorado, The, Boulder, Colo.

[21] Appl. No.: 443,958

[22] Filed: May 18, 1995

Related U.S. Application Data

[63] Continuation of Ser. No. 123,564, Sep. 20, 1993, abandoned.
[51] Int. Cl.⁶ ..................................................... C12P 19/34
[52] U.S. Cl. ........................................ 435/91.3; 435/91.5
[58] Field of Search ................................. 435/91.3, 91.5, 435/91.1

[56] References Cited

PUBLICATIONS

A.S. Spirin, in "Proceedings of Frontiers in Bioprocessing II," Boulder, Co, Jun. 17–21, Conference Proceedings Series (P. Todd, S.K. Sikdar and M. Bier, eds.), Amer. Chem. Soc., Washington, D.C. (1992).

Milligan et al., Nucleic Acids Res., vol. 15, No. 21, pp. 8783–8798, 1987.
Stratagene 1992 Product Catalog, p. 256, 1992.
Yolov et al. (1991), Bioorganiche skaya Xhimia 17(6): 789–794.
Fujita et al. (1993), Biotechniques 14(4): 608–617.
Arias et al. (1989), J. Biol. Chem. 264(6): 3223–3229.
Kigawa et al. (1991), J. Biochem. 110: 166–168.
Marble et al. (1993), Abstracts of Papers, 205th ACS National Meeting, Abstract BIOT 88.

*Primary Examiner*—David Guzo
*Attorney, Agent, or Firm*—Swanson & Bratschun LLC

[57] ABSTRACT

The instant invention provides a method for producing RNA enzymatically in a semi-batch or continuous-flow bioreactor using a DNA template immobilized to a solid support through a linkage having a single-stranded overhang extending from a noncoding strand. The coding strand remains dissociable from the immobilized noncoding strand. The immobilized RNA template is reused in at least sixteen rounds of transcription reaction. The coding strand can be replaced with a fresh DNA strand encoding the same or a different RNA.

46 Claims, 7 Drawing Sheets

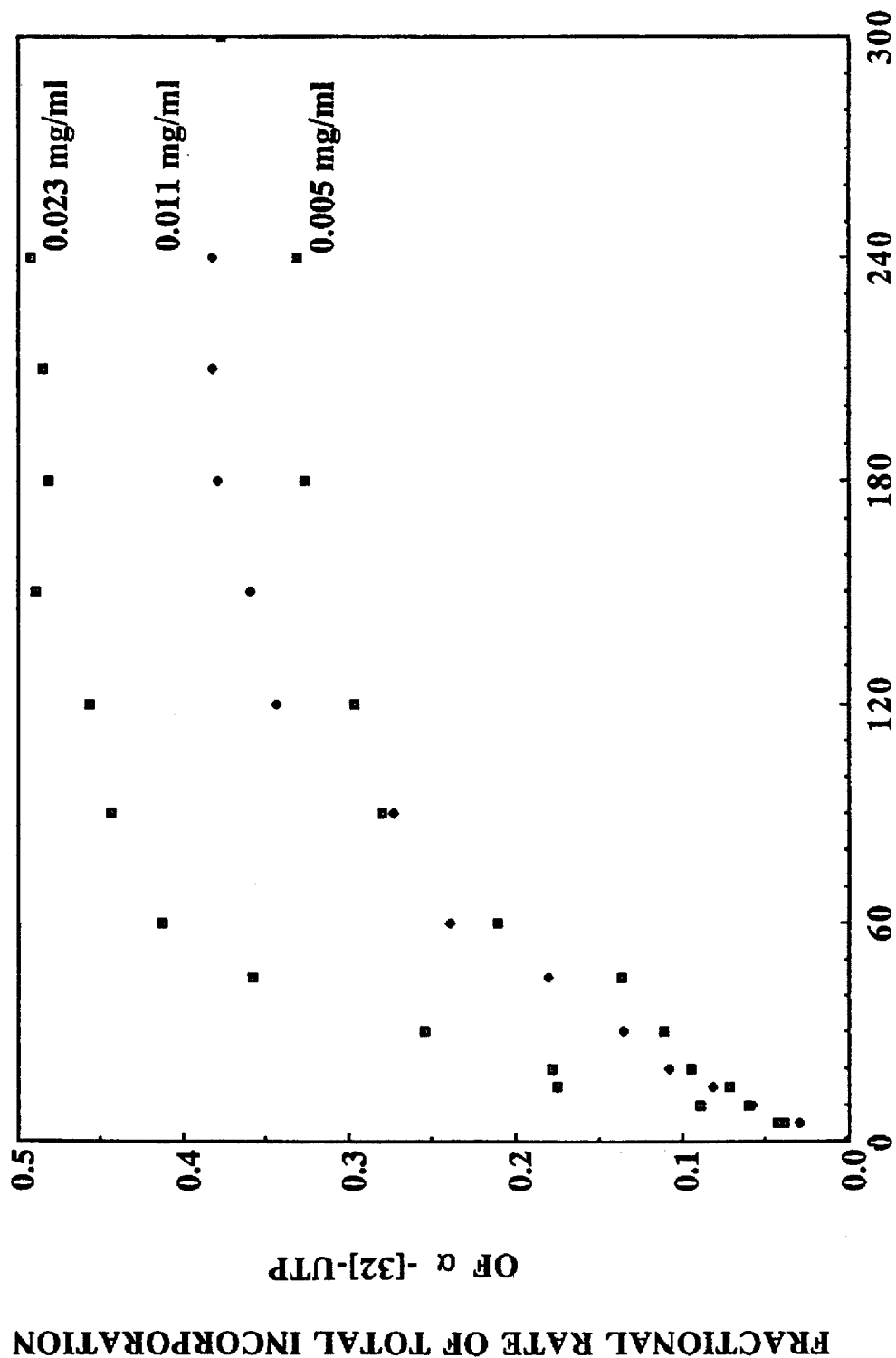

5,700,667

STRATEGY FOR THE PRODUCTION OF RNA FROM IMMOBILIZED TEMPLATES

This is a continuation of application Ser. No. 08/123,564 filed on Sep. 20, 1993, abandoned.

This work was partially supported by grants from the United States Government through the National Science Foundation. The United States Government may have certain rights in this invention.

FIELD OF THE INVENTION

The subject matter of the invention relates to enzymatic RNA synthesis on immobilized synthetic DNA templates in continuous-flow or semi-batch, stirred-cell bioreactors.

BACKGROUND OF THE INVENTION

Ribonucleic acid is an ubiquitous biopolymer integral to protein synthesis and cellular metabolism. It is generally composed of four basic monomers interlinked with phosphate diester linkages to form a directional (5'-3') polymer. In nature RNA exists in various lengths and shapes, ranging from short oligoribonucleotide primers for DNA synthesis to the very large ribosomal RNAs which form part of the translational machinery active during protein synthesis. The purine and pyrimidine bases of RNA interact via ring-stacking and hydrogen bonding networks to fold the polymer chains into compact structures containing surfaces capable of providing specific binding sites for a variety of ligands, including proteins, nucleic acids, divalent metal ions, and carbohydrates [Saenger, W. (1984) In *Principles of Nucleic Acid Structure* (C. R. Cantor, ed.) Chapters 6, 8, and 10. Spinger-Verlag, New York, N.Y.]. The 2'-hydroxyl group provides additional hydrogen bonding capacity and serves as a modest nucleophile in the presence of electropositive magnesium ions. In fact, some RNAs are capable of topologically juxtaposing surface recognition and catalysis elements to promote metal co-factor driven chemical reactions such as transesterification and phosphodiester bond hydrolysis [Cech, T. R. (1987) *Science* 236:1532–1539]. These sophisticated attributes have prompted investigators to pursue therapeutic applications based on RNA catalysis and specific ligand binding activities.

RNA is currently produced by either direct chemical or enzymatic synthesis at substantial cost. The former is assembled from the stepwise addition of fully protected, activated monomers in free solution (or on a solid support matrix) followed by chemical deprotection. The latter is obtained from cell-free, in vitro transcription using purified bacteriophage RNA polymerase, either plasmid or synthetic DNA templates, and ribonucleoside triphosphate precursors. Since both processes operate in a batch mode, massive production is limited by economy of scale. Chemical synthesis is favored for creation of short RNA species (less than twenty nucleotides in length), whereas enzymatic synthesis is preferred for larger molecules (ranging from twenty to several hundred bases in length). Enzymatic approaches appear more versatile since production costs do not appreciate linearly with increasing polymer length. In contrast, chemical synthesis yields decrease with increasing length due to the exponential effect of inefficient stepwise addition reactions.

Bacteriophage T7 RNA polymerase is a 98.5 KD, single polypeptide chain containing a magnesium-requiring, DNA-dependent, RNA synthesis activity [Chamberlin, M. and Ryan, T. (1982) In *The Enzymes* (P. D. Boyer, ed.), 3rd ed., Vol. 15, pp. 87–108, Academic Press, New York, N.Y.]. The enzyme specifically recognizes and binds to an eighteen base-paired double-stranded promoter region required for transcription initiation. The polymerase synthesizes RNA in the 5'-3' direction, consuming ribonucleoside triphosphate (NTP) precursors using DNA as a template. The nascent transcript forms a transient RNA/DNA hybrid mediated by Watson-Crick base pairs which continually form at its growing 3'-end. The enzyme displays temperature and pH optima at 37° C., pH 8.3 and requires a reducing agent to maintain one or more free (reduced) cysteine residues which are essential for transcriptional activity [Chamberlin and Ryan (1982) supra]. The enzyme has been cloned into and overexpressed in *E. coli*, from which it is subsequently purified to near homogeneity for cell-free, in vitro transcription applications [Davanloo, P.; Rosenberg, A. H.; Dunn, J. J.; and Studier, F. W. (1984) *Proc. Nat. Acd. Sci., USA* 81:2035–2039].

T7 RNA polymerase is active on double-stranded, T7 promoter-containing plasmid templates as well as synthetic DNA templates (composed of a double-stranded promoter region directly upstream of a single-stranded coding region [Milligan, J. F.; Groebe, D. R.; Witherell, G. W.; and Uhlenbeck, O. C. (1987) *Nuc. Acids Res.* 15:8783–8798]. The former are favored for synthesis of large RNA molecules (greater than fifty bases in length), whereas the latter are used for smaller RNA transcripts. Run-off in transcription from linearized plasmid templates proceeds with high fidelity, yielding one predominant RNA product species. In contrast, enzyme mediated synthesis from synthetic DNA templates is not as processive, yielding a distribution of products varying in size from short, premature, (abortive) transcripts to high molecular weight run-on (extended) RNAs. This complication requires downstream purification (denaturing polyacrylamide gel electrophoresis or high performance liquid chromatography) to afford the desired product devoid of contaminating RNA or DNA. Abortive transcripts arise from premature dissociation of RNA polymerase (or the nascent RNA transcript) from the active ternary complex. Run-on products presumably arise from template independent polymerization events which are believed to be promoted by the unusually high enzyme and substrate concentrations. In theory, one way to minimize abortive transcripts is to stabilize the active ternary complex from premature dissociation. Polyethylene glycol (MW 8,000) has been reported to stimulate transcription yields [Milligan et al. (1987) supra], presumably by lowering the chemical potential of the solvent species and thereby creating excluded volume effects which are thought to stabilize the ternary complex.

A material cost analysis reveals that the purified RNA polymerase is the most costly reaction component, followed by the DNA templates and NTPs, respectively. The cost of the remaining materials (transcription buffer components) are trivial in comparison. Furthermore, most protocols discard synthetic DNA templates (or remove them by enzymatic treatment) following a single batch reaction.

A method to synthesize small RNAs from 12 to 35 nucleotides in length using T7 RNA polymerase and synthetic DNA templates was reported by Milligan et al. (1987) supra. In this case, the reaction was carried out completely in solution phase. Chemically synthesized DNA templates comprising an 18 nucleotide coding region were not immobilized, but reacted freely in the reaction mix. The yields of full length transcripts varied substantially and extra bands corresponding to nontemplate encoded nucleotides were added to the end of the expected full length transcripts.

Arias and Dynan (1989) *J. Biol. Chem.* 264:3223–3229 synthesized run-off RNA transcripts of between 135 and 165 nucleotides using RNA polymerase II and a promoter-containing DNA template immobilized to a solid support via a biotin-streptavidin linkage at the 5'-end of the DNA fragment. In this study, biotinylated, promoter-containing DNA fragments were coupled to streptavidin-agarose beads which were added to the transcriptional reaction mixture to allow synthesis of detectible amounts of RNA.

The use of immobilized DNA templates as substrates for bacteriophage RNA polymerases were investigated by Fujita and Silver (1993) *BioTechniques* 14:608–617. Double-stranded DNA molecules with a T7 or T3 RNA polymerase promoter at one end and a single biotin moiety at the other end were attached to streptavidin-coated paramagnetic beads and used in transcription reactions. When the DNA was oriented so that transcription proceeded toward the bead and the DNA was attached by a biotin-dUTP or biotin-dATP moiety at the 3'-end of the nontemplate strand, the yield and quality of RNA synthesized was grossly equivalent to that made in solution after one hour of incubation. When the biotin moiety was placed at the same end of the template as the T7 promoter, very little RNA was synthesized. With DNA anchored to beads by a single 3'-biotin-dATP or -dUTP moiety, 7%–16% of the DNA was displaced during transcription. These losses appeared to be progressive on reuse of the bead-DNA complex; for one template, a 40% decrease in the amount of synthesized RNA was noted after three serial synthesis reactions. It was reported that the major unexpected result was that when the DNA was attached to the streptavidin beads by means of a 5'-biotin-phosphoramidite reagent, the DNA-bead complex was grossly unstable to the activity of the RNA polymerase.

Elov et al. (1991) *Bioorg. Khim.* 17:789–794 synthesized RNA using T7 RNA polymerase and immobilized DNA in a flow-through type reactor. A promoter-containing DNA fragment was covalently linked to a solid support (SEPHAROSE 4β or TOYOPEARL HW-55 from Toyo Soda, Japan) through the 3'-end of the lower (template) strand. The yields of RNA were approximately half that obtained on transcription of the same amount of DNA template in solution under the same conditions. The RNA produced was a mixture containing the desired 14-membered transcript, some larger products and a fairly large amount of shorter by-products 2–8 units long. A somewhat larger amount of short (as compared to the desired oligonucleotide length) by-products were obtained in the immobilized DNA system. The reaction was carried out in a reactor of the flow-through type which consisted of a column containing immobilized RNA template and equipped with in-flow and exit lines. A cycle of operations was followed: (a) the in-flow of a solution of reagents comprising nucleoside triphosphates and T7 RNA polymerase; (b) one hour incubation at 37° C.; and (c) discharge of the spent reaction solution comprising RNA transcripts produced. A fall in the yield of RNA on transcription of the immobilized DNA with time was observed.

The use of a bioreactor capable of operating in a continuous-flow mode has been reported for protein synthesis by Spirin (1990) *Proceedings of Frontiers in Bioprocessing II*, Boulder, Colo., June 17–21, Conference Proceedings Series (P. Todd, S. K. Sikdar, and M. Bier, eds.), *Amer. Chem. Soc.*, Washington, D.C. (1992). One type of bioreactor described by Spirin (1990), supra, operated using cell-free translation of mRNA templates in prokaryotic and eukaryotic cell lysates. Another type of bioreactor utilized coupled transcription-translation of DNA templates in solution phase. Both types of reactors were designed for efficient production of protein.

To date, although attempts have been made to synthesize RNA on immobilized RNA templates in laboratory experiments, there still remains a need or a method to produce RNA in large quantities, in continuous operations, at low cost and without requirement for laborious purifications at intermediate stages.

SUMMARY OF THE INVENTION

The present invention provides a method for the enzymatic synthesis of RNA through the use of immobilized DNA templates. The DNA template is immobilized to a solid support through a linkage comprising a single-stranded overhang extending from the noncoding strand. Also, the DNA template is immobilized to a solid support in such a manner that the DNA template remains dissociable and replaceable. The DNA template is shown to be reusable for up to at least sixteen cycles of the transcription reaction.

In a particular embodiment of the invention, the transcription reaction is carried out in a transcription reactor (bioreactor). The bioreactor is configured such that reactants are delivered via a feed line to the reactor core and RNA products are removed by passing through an ultrafiltration membrane (having a nominal molecular weight cut-off, e.g., 100,000 daltons) to the exit stream. The reactants comprise a viral RNA polymerase and nucleoside triphosphates or analogs thereof. The ultrafiltration membrane is composed of a low protein-binding polymer matrix and serves to selectively retain both the RNA polymerase and the immobilized DNA templates in the reactor core. The transcription reactor is operated in either semi-batch or continuous-flow modes. In general, bioreactors are set up to produce either short RNA species (from approximately twenty to approximately one hundred nucleotides in length) or RNA species greater than one hundred nucleotides in length.

The method of the invention utilizes DNA templates that are chemically synthesized oligonucleotides, isolated DNA restriction fragments (e.g., plasmid DNA) or amplified oligonucleotides, for example, from amplification procedures such as PCR (polymerase chain reaction), SELEX (Systematic Evolution of Ligands by Exponential Enrichment), NASBA (Nucleic Acids Sequence Based Amplifications), etc. These templates comprise a promoter sequence and a coding region. A DNA template can be a double-stranded duplex or a unit that comprises a double-stranded promoter region upstream of a single-stranded RNA coding region. It is further contemplated that a single stranded, DNA template in a hairpin configuration can be immobilized and utilized for RNA synthesis. Similarly, templates can be utilized in which the RNA coding strand is covalently linked to controlled pore glass supports. In the latter case, the DNA template can be chemically synthesized directly onto the controlled pore glass supports.

In a specific embodiment of the invention, immobilization of a DNA template to a solid support occurred through a noncovalent biotin-streptavidin interaction. The noncoding strand of the DNA template was modified with a 5'-terminal biotin group which functioned to immobilize the oligomer to a solid support matrix comprising streptavidin protein. The RNA coding strand remained nonimmobilized. This invention also contemplates immobilization of DNA templates to solid supports through other types of noncovalent linkages, e.g., poly(A)-poly(T), and poly(G)-poly(C) interactions, among others, as well as through covalent bonding, e.g., ester linkage or derivative thereof.

It is further contemplated by this invention that to immobilize a DNA template to a solid support consideration be given to optimizing the spatial separation of the template from the support. In a specific embodiment, space was provided by a single-stranded trinucleotide overhang between the upstream region of the DNA template and the biotin molecule. It is also contemplated that additional upstream gene sequences or additional promoter sequences may be inserted at the 5'-end of the DNA template.

It is further contemplated in the method of the invention that the DNA template be modular. The coding strand of DNA is not immobilized and is dissociable. The dissociated strand can be exchanged for a new DNA strand having the same or different coding sequence.

The instant invention also provides a bioreactor capable of producing RNA and separating the product from higher molecular weight reactants. The bioreactor is configured such that reactants are delivered through an input feed line to the reactor core and such that reaction products are removed by passing through an ultrafiltration membrane to the exit stream. The ultrafiltration membrane is composed of a low protein-binding polymer matrix and serves to selectively retain both the RNA polymerase and the immobilized DNA templates in the reactor core. RNA transcripts pass through the ultrafiltration membrane into the exit stream.

BRIEF DESCRIPTION OF DRAWINGS

FIG. 7 describes transcription at reduced enzyme concentrations. Data represent average values from two separate experiments. The cumulative total [$\alpha$-$^{32}$P]-UTP incorporation is plotted as a function of time.

DETAILED DESCRIPTION OF INVENTION

Figure 1:
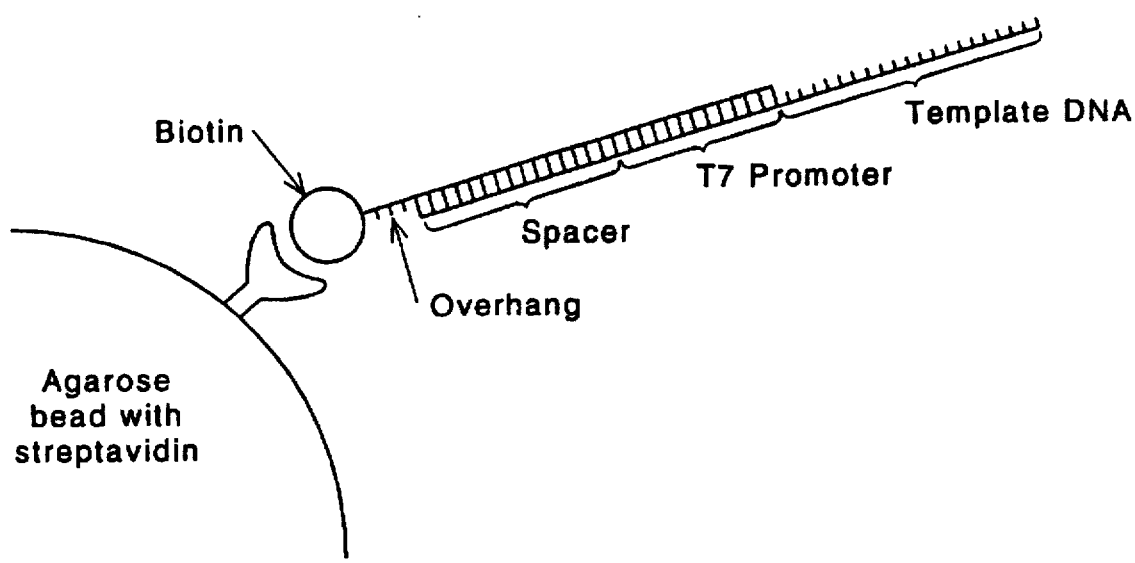
FIG. 1 is a scheme demonstrating immobilization of the DNA template to a solid support, in particular, the binding of biotin-DNA to streptavidin-coated agarose beads.

The following definitions are provided in order to provide clarity as to the intent or scope of their usage in the specification and claims.

The terms bioreactor or transcription reactor as used herein refers to a chamber or test tube or column wherein a transcriptional reaction is carried out under specified conditions. The bioreactor may be thermal regulated to maintain accurately a specific temperature, usually between 4° and 40°. The bioreactor may be configured with an inflow or feed line, an exit port, and may be fitted with an ultrafiltration membrane having a specific size limitation. The bioreactor may be a stirred-cell with provision for variable rates of stirring.

The term semi-batch as used herein refers to the operation of the transcription reaction as a repetitive series of transcription reactions. For example, the reaction is allowed to proceed for a finite time at which point the product is removed, new reactants added, and the complete reaction repeated.

The term continuous-flow as used herein refers to a reaction that is carried out continually in a bioreactor core with supplemental reactants constantly added at a fixed flow rate through an input feed line and products constantly removed at a fixed flow rate through an exit port.

The term short RNA species as used herein refers to RNA transcripts that are from approximately twenty to approximately one hundred nucleotides in length.

The term modular as used herein refers to a DNA template wherein the coding strand of the template is dissociable and can be replaced by a new DNA strand comprising the same or a different coding sequence.

A single-stranded overhang or overhang as used herein refers to a nucleotide sequence extension from a DNA template which is single-stranded and acts as a linker arm to provide adequate spatial separation of the template from the solid support. It is preferred that the overhang be from 1 to 500 bp in length, more preferably from 1 to 50 bp in length and most preferably from 2 to 20 bp in length.

The term linker as used herein refers to the linkage between a ligand and a DNA template strand. The chemistry of the linkage varies as a function of the method of preparation of the ligand-DNA construct. In a specific example, a biotin-DNA construct may be synthesized to comprise regions having different chemical compositions: (a) biotin-DNA with a hydrophilic tether, (b) biotin-DNA with a hydrophobic tether, and (c) biotin-DNA with an amphipathic tether.

The term tether as used herein refers to the chemical character of a region of the linkage formed between a ligand (e.g., biotin) and a DNA strand.

The term spacer as used herein refers to nucleotide sequences upstream of a first promoter region. Included within a spacer may be additional promoter regions, leader sequences, 5'- upstream gene regions acting in cis, enhancer elements, inducible elements, etc. A spacer may also comprise a run of nucleotides having undefined function to satisfy spatial demands.

The term a modified or a different coding region as used herein refers to a coding region which was modified partially or completely such that it encodes a different RNA sequence.

The term modified through chemical reaction or chemical engineering as used herein refers to protein modification which results from either direct manipulation of the protein or indirectly through modification of a nucleotide sequence encoding the given protein.

To date, for both commercial and experimental purposes, RNA synthesis is generally performed in solution using isolated or chemically synthesized DNA templates in solution phase. Such operations give low yields of RNA, are labor-intensive, utilize costly reagents (RNA polymerase, nucleoside triphosphates, expendable DNA templates, etc.) and produce a mixture of RNA and non-RNA products, which necessitates purification subsequent to synthesis.

Several attempts have been made to devise more efficient methods of synthesizing RNA. Arias et al. (1989) supra; Elov et al. (1991) supra; and Fujita et al. (1993) supra experimented with synthesis on solid supports using immobilized DNA templates. However, none of these references enabled a method of RNA synthesis that gave large yields of RNA, that produced an isolated RNA product and that was more cost-efficient. The present invention provides a method for the production of RNA such that a large amount of RNA is produced, such that the RNA product obtained is immediately separated from higher molecular weight components, eliminating the need for subsequent purification of RNA from higher molecular weight molecules, e.g., DNA, proteins, etc., and such that costly reagents are recycled or reused, thereby decreasing the cost of RNA production.

In one embodiment of the invention, the use of immobilized synthetic DNA templates was exploited for the production of short RNA species (twenty to fifty nucleotides in length) in a bioreactor (in both a test-tube and a stirred-cell transcription reactor). The synthetic DNA template consisted essentially of a double-stranded duplex attached to a single-stranded RNA coding region. In particular, the template contained two DNA molecules (with 36 and 61 nucleotides, respectively) which hybridized to form a unique thirty-three base pair hybrid, containing a T7 RNA polymerase consensus promoter sequence upstream of a single-stranded RNA coding region. The 5'-end of the top, non-coding strand (36-mer) was attached to a biotin with a hydrophobic tether. Two types of biotin-DNA constructs were utilized in the construction of DNA templates, e.g., a biotin-DNA with a hydrophobic tether (Genosys Biotechnologies, Inc. Woodlands, Tex.) and a biotin-DNA with a hydrophilic tether (Macromolecular Resources, Fort Collins, Colo.). The use of a biotin-DNA with an amphipathic tether is also contemplated by this invention.

The biotinylated DNA strand was then immobilized to agarose beads coated with streptavidin protein as illustrated in FIG. 1. The bottom, RNA-coding strand (61-mer) was unmodified and remained nonimmobilized. The template was designed such that the 5'-biotin moiety was followed by a single-stranded trinucleotide overhang which acted as a linker arm to provide adequate spatial separation of the template from the support. The length of the single-stranded overhang is variable and is optimized for the particular promoter sequence and RNA polymerase being utilized in the transcription reaction. It is preferred that an overhang be between 1 and 500 bp in length, more preferred from between 2 and 50 bp in length and most preferred from 2 and 20 bp in length.

This invention contemplates other types of immobilized DNA templates. A template may be comprised exclusively of a double-stranded duplex. Alternatively, a template may consist of a single-stranded hairpin template wherein the hairpin structure comprises a promoter sequence and is followed by a single-stranded coding region. A different embodiment of the invention contemplates a single-stranded solid-phase DNA template which can be activated by supplying the complementary promoter strand in solution to act in trans. A DNA template used in this invention may be modified with a ligand for immobilization to a solid support at the 5'-end, the 3'-end, or at an internal nucleotide of a DNA strand.

This invention also contemplates immobilization of DNA templates to solid supports through other types of noncovalent linkages known in the art, e.g., poly(A)-poly(T), poly(G)-poly(C), etc., as well as covalent linkages, e.g., ester linkages and derivatives thereof. Many types of solid support matrices (solid or porous) are known in the art including, but not limited to, polystyrene, latex microsphere, streptavidin-agarose beads, 3M EMPHASE (biosupport beads manufactured by the 3M Company) supports, streptavidin-paramagnetic particles, acrylic beads, SEPHAROSE, TOYOPEARL, and controlled pore glass.

It is further contemplated that a DNA template for the method of producing RNA of the invention comprises, in addition to a promoter sequence, a spacer region comprising nucleotide sequences upstream of the promoter sequence. The spacer region may include, singly or in plurality, an additional promoter sequence, a leader sequence, a 5'-upstream gene region acting in cis, an enhancer element, an inducible element, etc.

Figure 2:
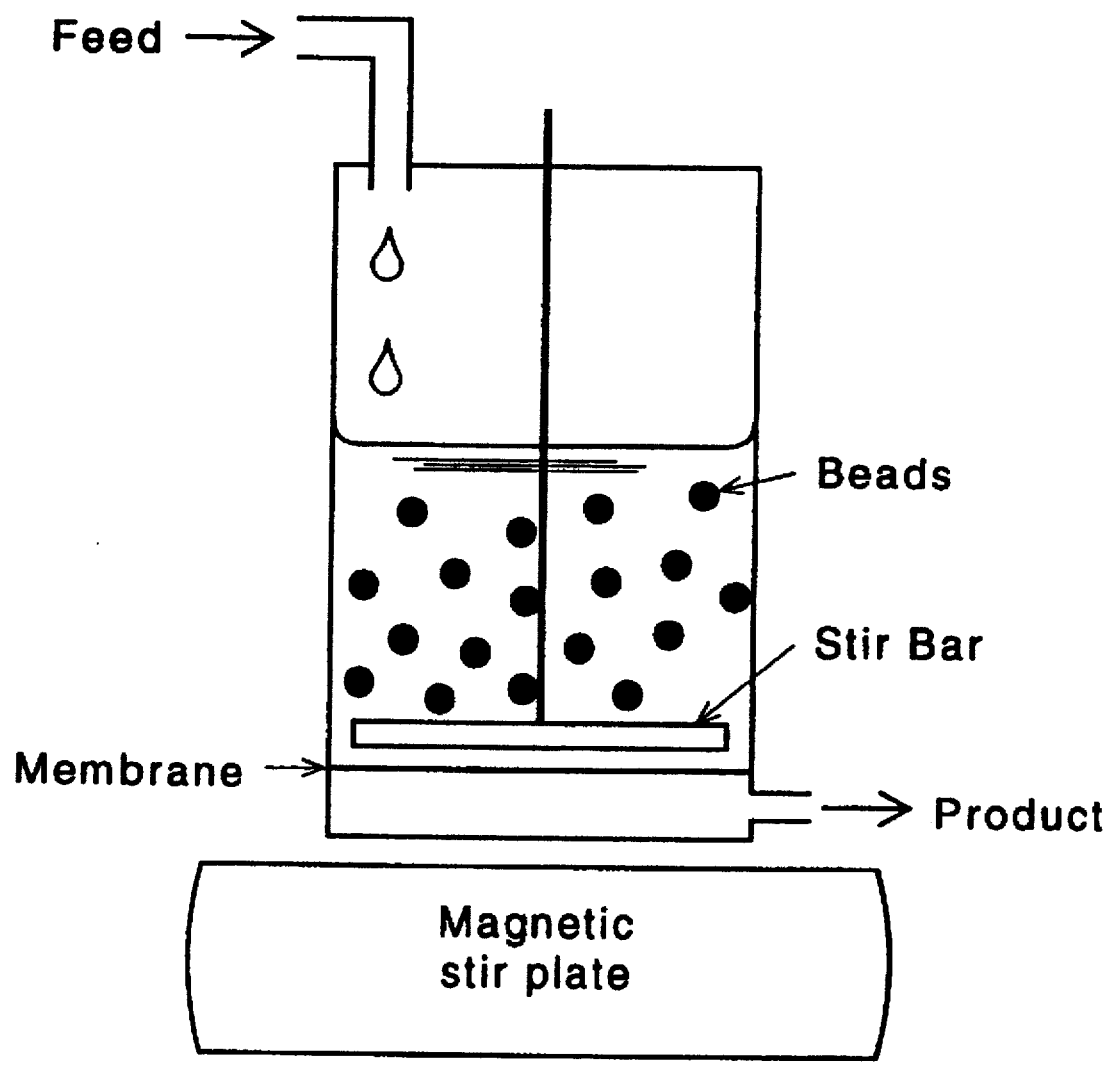
FIG. 2 is a schematic drawing of a semi-batch or continuous-flow, stir-cell reactor.

The invention contemplates the synthesis of RNA in a transcription reactor (bioreactor). The bioreactor was designed to be used either as a simple test-tube transcription reaction operating in a batch-mode, or as a stirred-cell, fluidized-bed reactor core (FIG. 2) configured such that reactants are delivered via a feed line to the reactor core and products are removed by passage through an exit line which may be fitted with a filtration (microfiltration or ultrafiltration) membrane having a molecular weight exclusion limitation (e.g. 100 kD). The filtration membrane is composed of a low protein-binding polymer matrix and serves to selectively retain both the RNA polymerase and the immobilized DNA templates in the reactor core. The reactants comprise a viral RNA promoter (e.g., T7, T3, SP6 RNA polymerase and active modifications thereof) and nucleoside triphosphates or analogs thereof, e.g., α-thio-nucleoside triphosphate, 2'-fluoro-nucleoside triphosphate and 2'-amino-nucleoside triphosphate. 2'-fluoro-and 2'amino-nucleoside triphosphate analogs have been reported to act as substrate for T7 RNA polymerase [Aurup et al. (1992) *Biochemistry* 31:9636–9641]. Other modified nucleoside triphosphates which can be specifically incorporated by natural or modified polymerases into RNA analogs are contemplated by the instant invention as substrates for RNA analog production.

Figure 3:
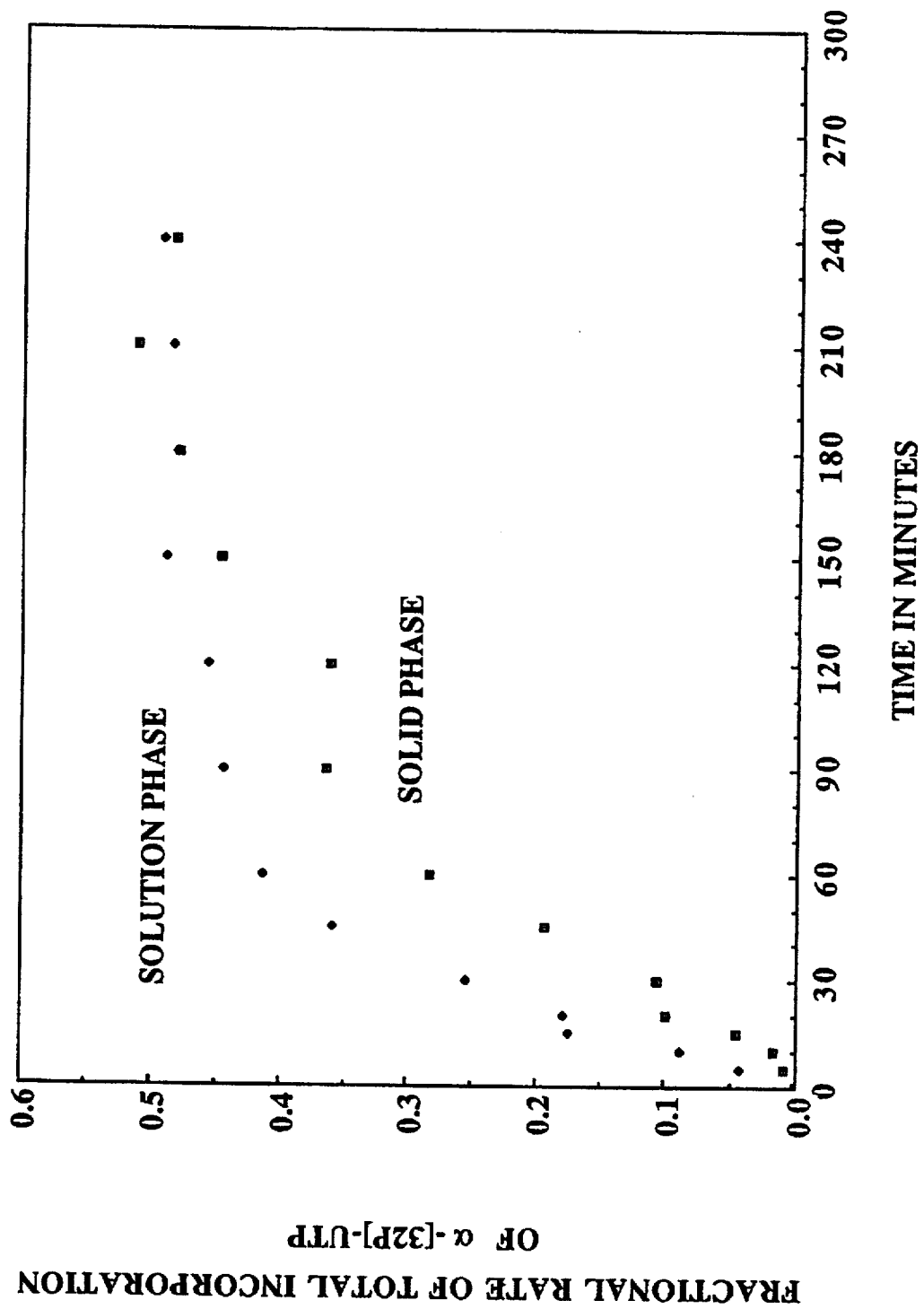
FIG. 3 presents a direct comparison of the transcriptional activities of solid and solution phase templates in batch reactions (100 µl volume). The cumulative [$\alpha$-$^{32}$P]-UTP incorporation is plotted as a function of time. The data consists of numerical averages obtained from two separate experiments.

Transcriptional activities of solid and solution phase templates in batch reactions were compared as shown in FIG. 3. In these studies the DNA template was immobilized using biotin-DNA with a hydrophobic tether. The immobilized DNA templates sustained transcription at approximately one-half the initial rate of their solution phase counterparts. Nevertheless, despite the reduced transcriptional initial rate for solid phase templates, equivalent yields of RNA were obtained when the reaction time period was doubled from two to four hours. In each case the reaction conditions were identical (1 μM DNA and 0.023 mg/ml T7 RNA polymerase), differed only by the presence or absence of a 5'-terminal biotin moiety.

Unexpected results were obtained when the same studies were conducted using a DNA template comprising a biotin-DNA with a hydrophilic tether. Under these conditions, the reaction kinetics were essentially the same for solid phase as for solution phase. The initial rate of reaction for the immobilized template having a biotin-DNA with a hydrophilic tether was the same as for the template in solution phase. The best mode for the transcriptional reaction appeared to be a DNA template wherein the immobilized DNA template carried a biotin-DNA with a hydrophilic linkage.

In general, immobilized DNA templates are retained in the stir-cell reactor, whereas solution phase templates (molecular weight 30 kilodaltons) are small enough to pass through the 100 kilodalton ultrafiltration membrane into the product stream. Consequently, it was expected that the solution phase templates would wash-out of the reactor during the course of the semi-batch transcription sequence. Since RNA product was detected up to four hours with a single dose of enzyme and up to 8 hours with a second enzyme supplement, it is possible that the solution phase templates did not wash-out of the reactor. This may be due in part to the specific binding of RNA polymerase to template molecules during transcription, forming complexes which are selectively retained by the membrane. Alternatively, solution phase templates may in fact wash-out during the course of the reaction. In this case, products observed at later timepoints may reflect RNA which was transcribed early on but not removed until subsequent timepoints.

Figure 4:
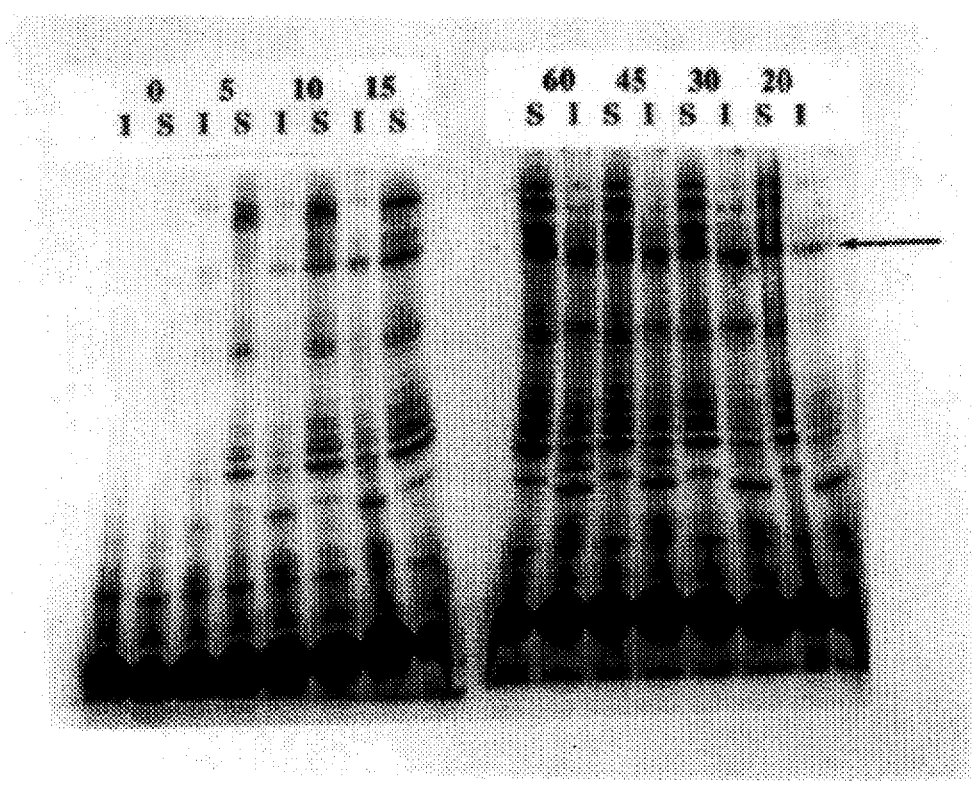
FIG. 4. Electrophoretic resolution of RNA products in phosphorescent gel image from transcription with solid (I) and solution (S) phase templates. The reaction sequence is composed from individual timepoints obtained during the first hour of the transcription. Electrophoresis separates molecules on the basis of their charge to mass ratio. Hence, unincorporated UTP accumulates at the bottom of each lane followed by RNA products of increasing nucleotide length.

RNA products from the transcription reaction with solid phase template differed in electrophoretic pattern (FIG. 4) from the pattern observed for the solution phase reaction. The pattern of abortive (premature) transcripts obtained from solid phase templates (using biotin-DNA with hydrophobic tether) was shifted down in size relative to solution phase reaction. Furthermore, the solution phase reaction appeared to generate more of the undesired run-on (extended) transcripts than the immobilized counterpart. The full-length RNA product is one of the few bands in common between the solution and solid phase reactions and is the most prominent RNA species in the reaction at sixty minutes (band position marked by the arrow in FIG. 4). Abortive transcripts are believed to arise from premature dissociation of RNA polymerase (or the nascent RNA transcript) from the active ternary complex. Run-on products presumably arise from template-independent polymerization events.

The observation that solid phase templates yielded lower amounts of undesired run-on transcripts was fortuitous and completely unexpected. The absence of contaminating run-on transcripts directly facilitates downstream purification and product recovery from electrophoresis gels or HPLC columns. Secondly, the reduction in run-on transcripts minimizes unwanted reaction byproducts, which ultimately increases the transcriptional efficiency of the desired RNA product species. Finally, the reduction in run-on transcripts implies a concomitant reduction in the release of inorganic pyrophosphate (released in every nucleotidyl-transfer reaction) associated with run-on RNA synthesis. Since inorganic pyrophosphate is a known inhibitor of T7 RNA polymerase activity, reaction efficiency can be improved by limiting its accumulation.

An advantage of the immobilized DNA template system over a corresponding solution phase reaction is that immobilized templates can be easily recovered from the crude reaction mixture for reuse in subsequent rounds of transcription reactions. Template reuse minimizes material costs and increases transcriptional productivity in terms of the number of transcripts generated per individual template molecule. Our initial results with an immobilized DNA template having a biotin-DNA with a hydrophobic tether indicated that solid phase DNA templates could be successively reused up to four times without detectable loss in activity, despite being washed (2×0.5 ml) with water between rounds of reaction. Continued use beyond four rounds ultimately resulted in decreased yields, presumably due to template instability. Since the template was composed of two separate strands held together by noncovalent hydrogen-bonding interactions, template dissociation is a realistic possibility.

Figure 5:
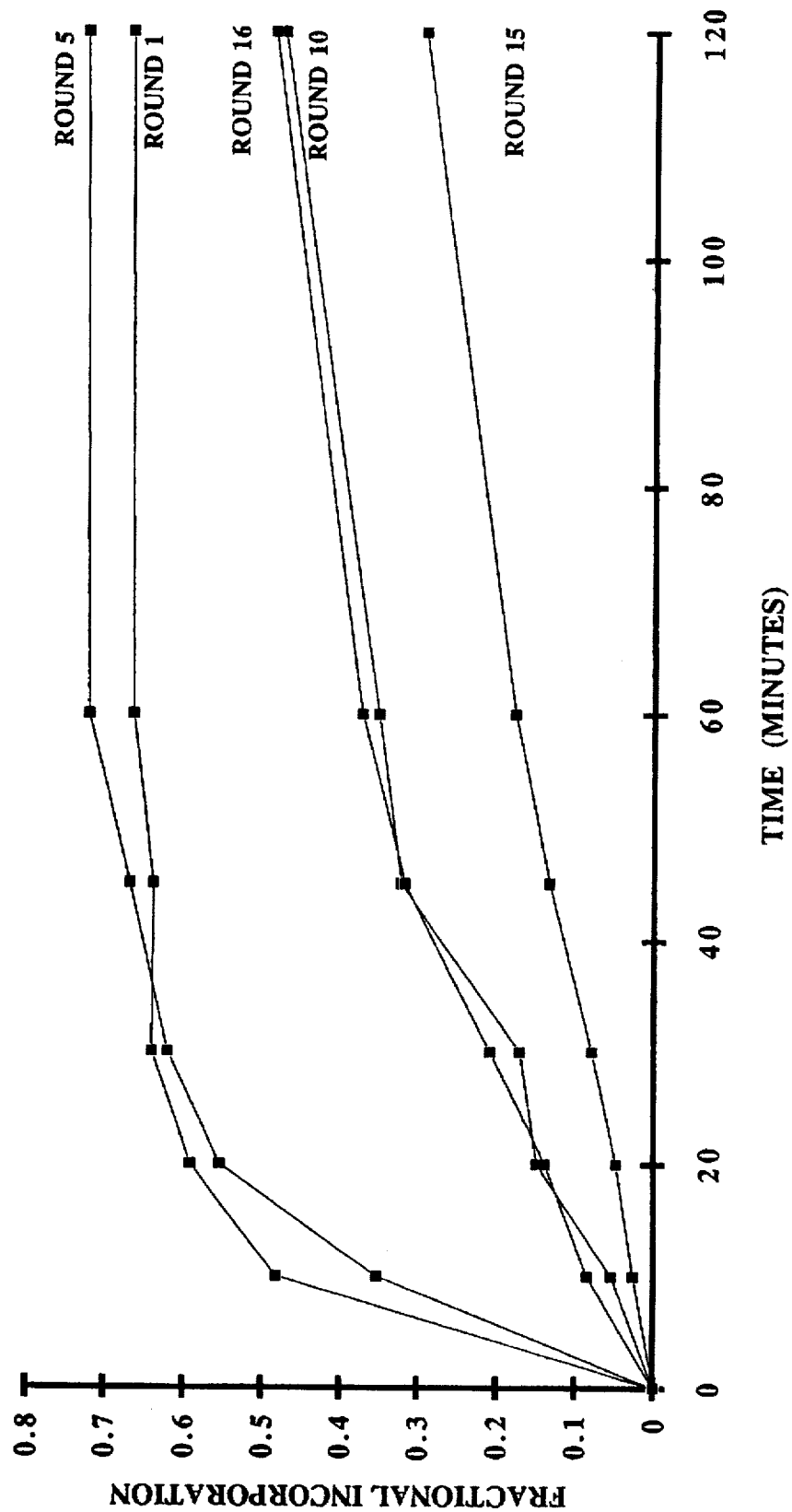
FIG. 5. Multiple reuse of immobilized DNA templates. Transcription is expressed as incorporation of $^{32}$P-UTP as a function of time. After each round of synthesis, fresh RNA polymerase, buffer, nucleoside triphosphates, etc., were added. The same immobilized DNA template was used for 15 rounds. Each round consists of 2 hours of incubation.
Figure 6:
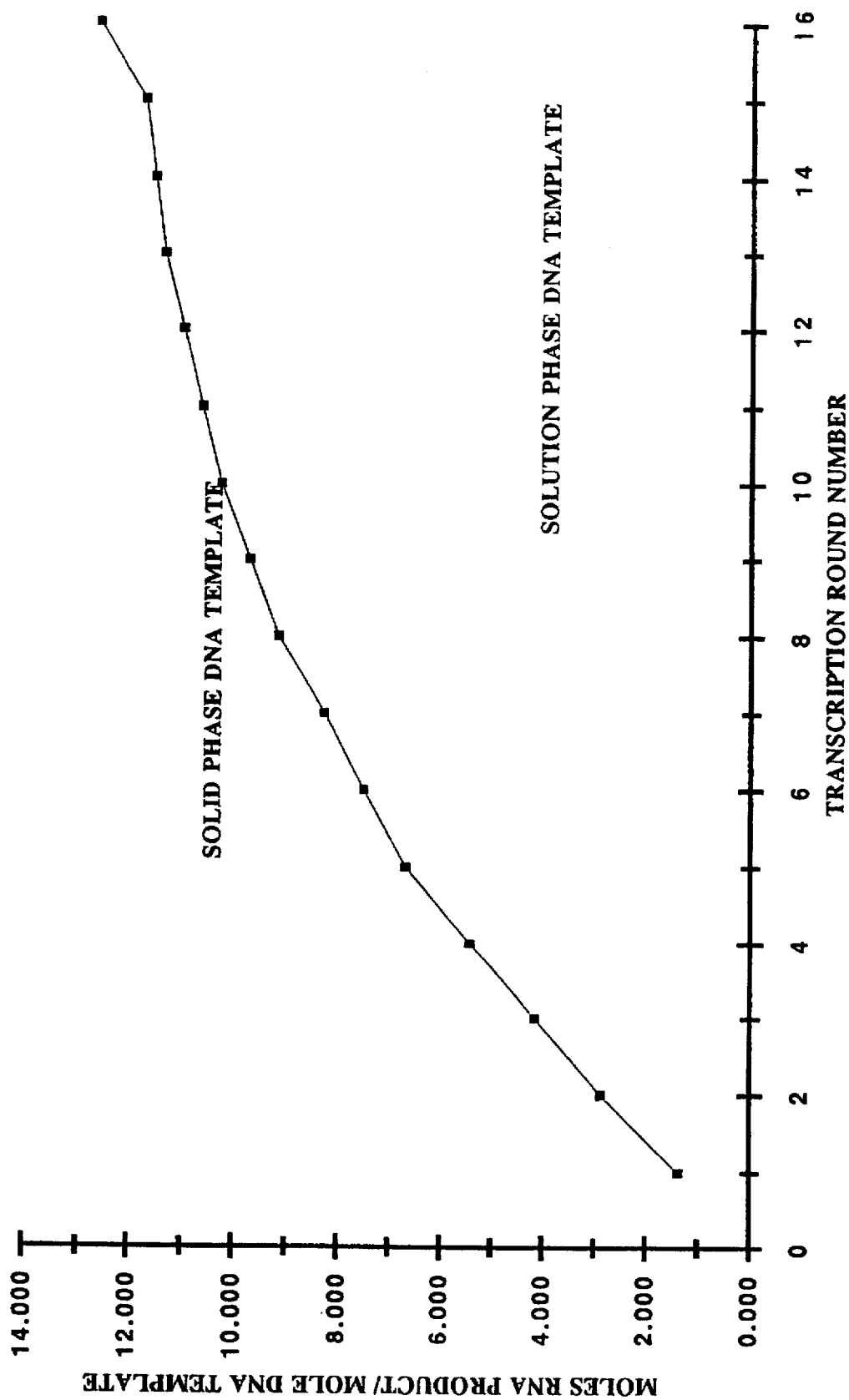
FIG. 6 presents the cumulative yield of the expected RNA 28-mer product as a function of increasing rounds of the transcription reaction. Yield is expressed as moles of RNA produced per mole of DNA template. The yield of RNA produced in a comparable solution phase reaction is indicated. After round 15, a fresh coding strand was added to the reaction mix, and the rate of reaction increased. A round of transcription reaction consists of 120 minutes of incubation.

More extensive reuse of immobilized DNA templates was observed in a system utilizing an immobilized DNA template having a biotin-DNA with a hydrophilic tether. In this system, the solid phase DNA templates could be successively reused up to five times without loss in activity and with modest reduction in activity and yield up to sixteen rounds (see FIG. 5). After each round of synthesis, fresh RNA polymerase, buffer and nucleoside triphosphates, etc., were added. However, the same immobilized DNA template was retained and reused for sixteen rounds. After the fifteenth round, the administration of a fresh bottom (coding) strand resulted in a resurgence of the rate of transcription. FIG. 6 illustrates the increasing yield of RNA from repetitive rounds of the transcription reaction from reuse of an original immobilized DNA template.

In order to assess the productivity of T7 RNA polymerase at reduced enzyme concentrations, a series of transcription reactions were performed using solution phase DNA templates. The time dependent increase of total RNA product formation was measured in duplicate at three separate enzyme concentrations [23 µg/ml, 11 µg/ml and 5 µg/ml] over the course of four hours. As shown in FIG. 7, each enzyme concentration curve was characterized by an initial linear phase which gradually plateaued, yielding a classic Monod curve. The slope of the initial enzyme velocities decreased proportionately (to a first approximation) with decreasing enzyme concentration. However, at longer timepoints, the overall productivity did not decrease proportionately with enzyme concentration. This suggests that the enzyme remains active for extended reaction times, ultimately yielding increased RNA production per polymerase molecule. This is evidenced by the fact that at 23 µg/ml the extent of UTP conversion reached fifty percent, whereas at 6 µg/ml thirty percent conversion was attained. Since the only variable in this study was enzyme concentration, other factors can be ruled out. Consequently, these results suggest that T7 RNA polymerase productivity can be increased by reducing the enzyme concentration and allowing the reaction to proceed for extended time periods. This is significant because standard transcription protocols of the prior art recommend enzyme concentrations ranging from 0.5 to 0.1 mg/ml.

In another embodiment of the invention, the application of immobilized DNA templates to preparative transcription reactions was carried out in a 1.0 ml volume, stirred-cell reactor operated in semi-batch mode and the ability to reuse the DNA templates was again established. Immobilized templates were active in successive rounds of semi-batch transcription reactions, but the yields were lower. Also, transcriptional activity from immobilized DNA templates could be rescued by adding an additional dose of fresh enzyme. Immobilized DNA templates were found to be active, stable and reusable in semi-batch transcriptional applications.

Except as noted hereafter, standard techniques for DNA chemical synthesis, isolation and purification of proteins and protein fragments, sequencing, chromatography, cloning, DNA isolation, amplification and purification, RNA isolation and purification, for enzymatic reactions involving DNA ligase, DNA and RNA polymerases, restriction endonuclease and the like, the PCR, SELEX, NASBA amplification techniques and various protein separation and purification techniques are those known and commonly employed by those skilled in the art. A number of standard techniques are described in [*Chemical and Enzymatic Synthesis of Gene Fragments* (H. G. Gassen and A. Lang, eds.) Verlag Chemie, Weinheim; Deerfield Beach, Fla.; Basel (1982)]; Deutscher (1990) Methods in Enzymology 182:309–539; Maniatis et al. (1982) *Molecular Cloning*, Cold Spring Harbor Laboratory, Cold Spring Harbor, N.Y.; Wu (ed.) (1979) Meth. Enzymol. 68; Sambrook, et al. (1989) *Molecular Cloning: A Laboratory Manual*, Second Edition, Cold Spring Harbor Press, N.Y.; Wu et al. (1983) Meth. Enzymol. 100 and 101; Grossman and Moldave (eds.) (1980) Meth. Enzymol. 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Method of Molecular Biology*; Glover (ed.) (1985) *DNA Cloning* Vols. I and II, IRL Press, Oxford, UK; Hames and Higgins (eds.) (1985) *Nucleic Acid Hybridization*, IRL Press, Oxford UK; Setlow, Hollaender (1979) *Genetic Engineering: Principles and Methods*, Vols. 1–4, Plenum Press, New York and Deutscher (ed.) (1990) *Guide to Protein Purification*, Academic Press, New York. Abbreviations and nomenclature, where employed, are deemed standard in the field and commonly used in professional journals such as those cited herein.

It will be appreciated by those of ordinary skill in the art that the objects of this invention can be achieved without the expense of undue experimentation using well known variants, modifications, or equivalents of the methods and techniques described herein. The skilled artisan will also appreciate that alternative means, other than those specifically described, are available in the art to attain nucleic acid synthesis and to achieve the functional features of the molecules described herein and how to employ those alternatives to achieve functional equivalents of the molecules of the present invention. It is intended that the present invention include those variants, modifications, alternatives, and equivalents which are appreciated by the skilled artisan and encompassed by the spirit and scope of the present disclosure.

The following examples are provided for illustrative purposes only and are not intended to limit the scope of the invention.

EXAMPLE 1

DNA Template Immobilization

Synthetic DNA molecules were prepared by Genosys Biotechnologies, Inc. (The Woodlands, Tex.), using conventional phosphoramidite chemistry. The transcriptional template codes for a 28-nucleotide pseudo-knot RNA molecule which specifically binds to the human immunodeficiency virus reverse transcriptase (HIV RT) primer binding site. The template consists of two DNA molecules (36 and 61 nucleotides, respectively) which hybridize to form a unique thirty-three base pair hybrid, containing a class II T7 consensus promoter sequence upstream of a single-stranded RNA coding region. The top strand (36-mer) is modified with a 5'-terminal biotin. Different types of biotin-DNA constructs can be synthesized, e.g., a biotin-DNA with a hydrophobic tether (Genosys Biotechnologies, Inc., Woodlands, Tex.), a biotin-DNA with a hydrophilic tether (Macromolecular Resources, Fort Collins, Colo.), and a biotin-DNA with an amphipathic tether. The biotinylated DNA is immobilized through the biotin moiety to a solid support matrix which contains streptavidin protein, while the RNA coding (bottom) strand (61-mer) remains unmodified. The template was designed such that the 5'-biotin moiety is followed by a single-stranded trinucleotide overhang which acts as a linker arm to provide adequate spatial separation of the template from the support. The equilibrium dissociation constant of the biotin-streptavidin complex is extremely low ($10^{-15}$M), resulting in high affinity binding, despite the noncovalent nature of the interaction.

Immobilized templates were prepared by adding 7,500 picomoles of purified 5'-biotin DNA (36-mer) to 1.0 ml of a 50% (v/v) solution containing streptavidin-coated agarose beads in 0.02% sodium azide (Pierce Immunochemicals, Rockford, Ill.) and incubating overnight at 4° C. with gentle mixing. The supernatant was removed and the beads were washed successively (4×0.5 ml) with sterile, deionized water. The unbound DNA in the original supernatant and the subsequent washes were quantified spectrophotometrically (260 nm or λmax) to determine the amount of 5'-biotin DNA remaining on support. Typically, 6,000 to 7,000 picomoles of DNA remain bound, corresponding to a DNA concentration of 12 to 14 μM on the surface of the beads. Since the support contains 1.5 mg of streptavidin/ml of beads, the maximal theoretical biotin binding capacity is calculated to be 50 μM (based on 4:1 biotin/streptavidin binding stoichiometry).

The immobilized top strand is then incubated (overnight at 4° C.) with a 1.5 molar excess of the bottom RNA coding strand (61-mer) to form the active template. Following DNA hybridization, the support is washed (3×0.5 ml sterile, deionized water) and quantified for the presence of unbound DNA. Solid phase templates are stored at 4° C. in 0.02% sodium azide (preservative) until further use. In practice, we find that immobilized DNA templates are stable for periods of several months without detectable loss of transcriptional activity.

EXAMPLE 2

Batch Mode Transcription Reactions

Transcription was assayed by the incorporation of radioactively labeled uridine triphosphate ([α-$^{32}$P]-UTP, 800 Curies/millimole, DuPont/NEN; Wilmington, Del.) into RNA products at physiological temperature. Small-scale (100 μl) transcription reactions were performed using either solution or solid phase DNA templates and standard reaction conditions (described below), except that polyethylene glycol was omitted from all reactions. Timepoints (5 μl reaction aliquots) were removed at successive intervals, quenched on ice with 75% deionized formamide and loaded onto 20% (19:1 crosslinking) denaturing (8M urea) polyacrylamide gels for electrophoresis (600 Volts, 15 milliamps, for 3 hours). The gel-fractionated RNA products were visualized and the radioactivity was quantified using a phosphorescent imager system (Molecular Dynamics; Sunnyvale, Calif.).

Transcription Reaction Mixture

| | |
|---|---|
| 40 mM Tris-HCl (pH 8.1) | 1 mM Adenosine Triphosphate |
| 20 mM Magnesium Chloride | 1 mM Cytosine Triphosphate |
| 5 mM Dithiothreitol | 1 mM Guanosine Triphosphate |
| 1 mM Spermidine-HCl | 0.1 mM Uridine Triphosphate |
| 0.01% Triton X-100 | 0.125 μM[α-$^{32}$P]-UTP (10 μCi) |
| 1 μM DNA Template | 0.023 mg/ml T7 RNA Polymerase |

EXAMPLE 3

Semi-Batch, Stirred-Cell Transcription Reactions

Preparative scale (1.0 ml) transcription reactions were performed in a stirred-cell reactor (Amicon; Beverly, Mass.)

operated in semi-batch mode, using either solution phase or immobilized DNA templates (1 µM reaction concentration). The stir-cell was equipped with a low protein-binding, ultrafiltration membrane (Amicon YM100) of nominal molecular weight cut-off 100,000 daltons. Sterile techniques were maintained to eliminate potential ribonuclease or bacterial contamination.

The transcription reaction conditions were identical to those listed above, except that the concentration of each NTP was 1 mM and no radioactivity was used. The stir-cell was loaded with a 1.0 ml reaction mixture and T7 RNA polymerase (0.023 mg/ml in reaction) was added at time zero. The reaction was allowed to incubate (37° C.) for one hour on a magnetic stirrer (low spin setting), prior to the removal of the first aliquot (0.5 ml) from the exit line. Upon product removal, the reaction was supplemented with additional transcription buffer containing 1 mM NTPs (0.5 ml), and the reaction was allowed to proceed for another hour. This semi-batch reaction cycle was performed for 8 consecutive hours, using the same DNA templates and without changing the ultrafiltration membrane and with 0.5 ml aliquots removed from the exit line every hour. Fresh enzyme (0.023 mg/ml) was added along with the buffer and NTPs midway through the reaction (4 hour timepoint).

Transcriptional activity was assayed qualitatively by fractionating RNA products on 20% (19:1 crosslinking) denaturing (8M urea) polyacrylamide gels, and staining overnight with stains-all dye (Sigma Chemical Co.; St. Louis, Mo.). RNA products were visualized by ultraviolet shadowing on 254 nm fluorescent thin layer chromatography plates and excised using a sterile razor blade for subsequent elution. Eluent was worked up and concentrated by three consecutive rounds of precipitation with ethanol prior to quantification via scanning UV spectrophotometry.

EXAMPLE 4

RNA Synthesis on Hairpin DNA Template

Single-stranded, hairpin DNA templates immobilized via biotin modifications (terminal or internal) may be particularly useful if template instability due to denaturation is a problem. Single-stranded hairpin templates are unique since they provide a double-stranded promoter region (required for RNA polymerase binding and initiation) followed by a single-stranded coding region, and yet, the whole structure is composed of only one DNA strand. Hairpin templates can be derivatized using conventional biotin-phosphoramidite chemistry [Winnacker and Dörper (1982) in Chemical and Enzymatic Synthesis of Gene Fragments (H. G. Gassen and A. Lang, eds.) Verlag Chemie, Weinheim, Deerfield, Fla., Basel], to contain 5'-terminal, 3'-terminal, or internal biotin moieties which can be subsequently immobilized onto streptavidin containing support matrices. In such a structure, instability due to nucleic acid denaturation (helix-coil transition) would be reduced by the presence of intramolecular Watson-Crick base pair interactions.

EXAMPLE 5

DNA Template Immobilization on Controlled Pore Glass

In order to facilitate preparation of immobilized DNA, it is convenient to use templates in which the DNA is covalently linked to controlled pore glass (CPG) via a 3'-0-succinyl-ester (bottom RNA coding strand). Since controlled pore glass is commonly used as a matrix support for solid phase chemical DNA synthesis [*Chemical and Enzymatic Synthesis of Gene Fragments* (H. G. Gassen and A. Lang, eds.) Verlag Chemie, Weinheim; Deerfield Beach, Fla.; Basel (1982)], direct use of such immobilized templates would further minimize preparation time and costs by eliminating the need for oligonucleotide purification, modification (5'-biotin) and subsequent immobilization. Covalently linked templates are activated by hybridizing the complementary T7 promoter, top-strand (supplied in solution) directly to the covalently linked RNA coding (bottom) strand.

An advantage of using CPG is that the pores are designed to maximize mass transfer of solvents used in DNA synthesis. The amount of the DNA loaded onto CPG is controlled in order to minimize steric crowding of the immobilized DNA system. Preferably, RNA coding strand is covalently immobilized, ensuring that it will remain associated with the solid support and not wash-out in a bioreactor setting.

We claim:

1. A method of producing RNA enzymatically in a bioreactor comprising the steps of:
    (a) immobilizing a DNA template, comprising a noncoding strand and a coding strand comprising a double-stranded promoter sequence and a double-stranded spacer sequence upstream of said promoter sequence, to a solid support through a linkage comprising a single-stranded overhang extending from the 5'-end of said noncoding strand and such that said coding strand remains dissociable from said noncoding strand;
    (b) contacting said immobilized DNA template of step (a) with a transcription reaction mixture comprising a buffer, nucleoside triphosphates and an RNA polymerase such that RNA having a sequence complementary to said coding strand is produced;
    (c) removing said RNA produced in step (b); and,
    (d) repeating steps (b) and (c).

2. The method of producing RNA of claim 1 wherein said single-stranded overhang is a nucleotide sequence of between 1 and 50 bp in length.

3. The method of producing RNA of claim 1 wherein said immobilization of said DNA template to said solid support occurs through a noncovalent linkage.

4. The method of producing RNA of claim 1 wherein said immobilization of said DNA template to said solid support occurs through a covalent linkage.

5. The method of producing RNA of claim 1 wherein the 5'-end of said noncoding DNA strand is immobilized.

6. The method of producing RNA of claim 1 wherein said immobilized DNA template comprises a two-stranded duplex comprising a spacer sequence and a promoter sequence followed by a single stranded coding region.

7. The method of producing RNA of claim 1 wherein said immobilized DNA template comprises a two-stranded duplex comprising a spacer sequence and a promoter sequence followed by two strands of coding region.

8. The method of producing RNA of claim 1 wherein said DNA template is obtained from a source of DNA selected from the group consisting of a chemically synthesized oligonucleotide, an isolated DNA fragment and an amplified DNA oligonucleotide.

9. The method of producing RNA of claim 1 wherein said spacer sequence comprises a plurality of promoter sequences.

10. The method of producing RNA of claim 1 wherein said spacer sequence comprises a 5'-upstream gene region.

11. The method of producing RNA of claim 1 wherein said spacer sequence comprises a plurality of 5'-upstream gene regions.

12. The method of producing RNA of claim 1 wherein said noncoding strand is modified at one end with a biotin moiety such that said biotin linked to DNA is selected from the group consisting of a biotin-DNA with a hydrophobic tether, a biotin-DNA with a hydrophilic tether and a biotin-DNA with an amphipathic tether.

13. The method of producing RNA of claim 1 further comprising:
    (e) replacing said coding strand with a new DNA strand comprising said coding region; and
    (f) repeating steps (b), (c) and (d).

14. The method of producing RNA of claim 1 wherein said coding strand is replaced by a new DNA strand comprising a modified or a different coding strand.

15. The method of producing RNA of claim 1 wherein said coding strand is replaced by a new DNA strand comprising multiple coding strand.

16. The method of producing RNA of claim 1 wherein said solid support is selected from the group consisting of polystyrene, latex microsphere, streptavidin-coated agarose beads, 3M EMPHASE supports, streptavidin-coated paramagnetic particles, acrylic beads, SEPHAROSE, TOYOPEARL, and controlled pore glass.

17. The method of producing RNA of claim 1 wherein said solid support is streptavidin-coated agarose beads.

18. The method of producing RNA of claim 1 wherein said RNA polymerase is selected from the group consisting of T7, T3, and SP6 RNA polymerases and said promoter sequence is a promoter of T7, T3, or SP6 bacteriophage, respectively.

19. The method of producing RNA of claim 1 wherein said nucleoside triphosphates are nucleoside triphosphate analogs.

20. The method of producing RNA of claim 1 wherein said method operates in a semi-batch mode.

21. The method of producing RNA of claim 1 wherein said method operates in a continuous mode.

22. The method of producing RNA of claim 1 wherein said bioreactor is a continuous flow stir-cell transcription reactor.

23. The method of producing RNA of claim 1 wherein said coding strand is dissociated from said immobilized DNA template, is removed from said transcription reaction mix and is replaced with a new coding strand.

24. The method of producing RNA of claim 1 wherein said coding strand is present in excess over said noncoding strand.

25. The method of producing RNA of claim 2 wherein said nucleotide sequence is between 2 and 20 bp in length.

26. The method of producing RNA of claim 1 wherein said single-stranded overhang is a nucleotide sequence of between 1 and 500 bp in length.

27. The method of producing RNA of claim 3 wherein said noncovalent linkage is a biotin-streptavidin linkage.

28. The method of producing RNA of claim 3 wherein said noncovalent linkage is selected from a group consisting of a poly(A)-poly(T) linkage and poly(G)-poly(C) linkage.

29. The method of producing RNA of claim 12 wherein said biotin linked to a DNA is a biotin-DNA with a hydrophilic tether.

30. The method of producing RNA of claim 18 wherein said RNA polymerase is expressed in a bacterium selected from the group consisting of Escherichia, Bacillus, Salmonella, and Pseudomonas.

31. The method of producing RNA of claim 19 wherein said nucleoside triphosphate analogs are selected from the group consisting of α-thio-nucleoside triphosphate, 2'-amino-nucleoside triphosphate and 2'-fluoro-nucleoside triphosphate.

32. The method of producing RNA of claim 22 wherein said stir-cell transcription reactor comprises a filtration membrane.

33. The method of producing RNA of claim 22 wherein said stir-cell transcription reactor comprises an inflow feed line and an exit port.

34. The method of producing RNA of claim 33 wherein said exit port comprises a filtration membrane.

35. The method of producing RNA of claim 34 wherein said filtration membrane is selected from the group consisting of a microfiltration and ultrafiltration membrane.

36. A method of producing RNA enzymatically in a bioreactor comprising the steps of:
    (a) immobilizing from the 5'-end a single-stranded, hairpin DNA template, comprising a single-stranded overhang, a spacer sequence a promoter sequence and a coding sequence, to a solid support;
    (b) contacting said immobilized DNA template of step (a) with a transcription reaction mixture comprising a buffer, nucleoside triphosphates and an RNA polymerase such that RNA is produced;
    (c) removing said RNA produced in step (b); and,
    (d) optionally, repeating steps (b) and (c).

37. The method of producing RNA of claim 36 wherein said single-stranded hairpin DNA template is immobilized to a solid support at a nucleotide position selected from a group consisting of the 5'-end, the 3'-end and an internal nucleotide position.

38. The method of producing RNA of claim 36 wherein said DNA template is immobilized through a noncovalent linkage.

39. The method of producing RNA of claim 36 wherein said DNA template is immobilized through a covalent linkage.

40. The method of producing RNA of claim 38 wherein said DNA template is immobilized through a biotin-streptavidin linkage.

41. The method of producing RNA of claim 39 wherein said DNA template is immobilized through a succinyl-3'-0-ester linkage.

42. A method of producing RNA enzymatically comprising the steps of:
    (a) immobilizing a single-stranded DNA template, to a controlled pore glass support such that the 3'-end of said DNA template is covalently linked to said controlled pore glass support using succinyl-3'-0-ester chemistry;
    (b) contacting said immobilized single-stranded DNA template of step (a) with a transcription reaction mixture comprising a complementary spacer and promoter strand, a buffer, nucleoside triphosphates and an RNA polymerase such that RNA is produced.

43. The method of producing RNA of claim 42 wherein said DNA template is chemically synthesized on said controlled pore glass support.

44. The method of producing RNA of claim 42 wherein said method is operated in a mode selected from a group consisting of a semi-batch mode or a continuous-flow mode.

45. The method of producing RNA of claim 42 wherein said immobilized DNA template is reused in successive rounds of transcription reaction.

46. The method of producing RNA of claim 42 wherein said DNA template comprises two DNA strands.

* * * * *